(12) United States Patent
Altmann et al.

(10) Patent No.: US 8,730,011 B2
(45) Date of Patent: *May 20, 2014

(54) WIRELESS POSITION TRANSDUCER WITH DIGITAL SIGNALING

(75) Inventors: Andres Claudio Altmann, Haifa (IL);
Assaf Govari, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1964 days.

This patent is subject to a terminal disclaimer.

(21) Appl. No.: 11/181,256

(22) Filed: Jul. 14, 2005

(65) Prior Publication Data

US 2007/0013540 A1    Jan. 18, 2007

(51) Int. Cl.
G08B 5/22    (2006.01)

(52) U.S. Cl.
USPC ............ 340/8.1; 600/300; 600/309; 600/424; 600/437; 600/485

(58) Field of Classification Search
USPC ................ 600/309, 437, 562; 606/1, 32; 340/572.1, 686.2, 8.1; 378/170
See application file for complete search history.

(56) References Cited

U.S. PATENT DOCUMENTS

| | | |
|---|---|---|
| 5,099,845 A | 3/1992 | Besz et al. |
| 5,391,199 A | 2/1995 | Ben-Haim |
| 5,443,489 A | 8/1995 | Ben-Haim |
| 5,762,064 A | 6/1998 | Polvani |
| 6,239,724 B1 | 5/2001 | Doron et al. |
| 6,349,116 B1 | 2/2002 | Hash et al. |
| 6,534,970 B1 * | 3/2003 | Ely et al. .................. 324/207.17 |
| 6,686,881 B1 | 2/2004 | Lu et al. |
| 6,690,963 B2 | 2/2004 | Ben-Haim et al. |
| 6,898,299 B1 * | 5/2005 | Brooks ......................... 382/115 |
| 7,518,518 B2 * | 4/2009 | Homanfar et al. .......... 340/572.1 |
| 7,585,302 B2 * | 9/2009 | Revie et al. .................... 606/129 |
| 7,817,040 B2 * | 10/2010 | Homanfar et al. .......... 340/572.1 |
| 8,000,772 B2 * | 8/2011 | Govari et al. ................. 600/424 |
| 2001/0051766 A1 * | 12/2001 | Gazdzinski .................... 600/309 |
| 2002/0065455 A1 | 5/2002 | Ben-Haim et al. |

(Continued)

FOREIGN PATENT DOCUMENTS

EP    1 321 097 A    6/2003
EP    1 552 795 B1    7/2005

(Continued)

OTHER PUBLICATIONS

EP Search Report No. EP 06 25 3675 Dated Feb. 9, 2009.

(Continued)

*Primary Examiner* — Baisakhi Roy
(74) *Attorney, Agent, or Firm* — Louis J. Capezzuto (57) ABSTRACT

Apparatus for tracking an object includes a position transducer, which is adapted to be fixed to the object. The position transducer includes a digital microcontroller, which includes a plurality of output pins, and which is operative to generate an alternating digital output at a selected frequency on at least one of the output pins. At least one transmit antenna is coupled directly to the at least one of the output pins, so that the at least one antenna transmits a magnetic field at the selected frequency responsively to the alternating digital output. A field sensor senses the magnetic field and generates a signal responsively thereto. A processor receives and processes the signal in order to determine coordinates of the position transducer.

41 Claims, 5 Drawing Sheets

(56) References Cited

U.S. PATENT DOCUMENTS

| | | |
|---|---|---|
| 2003/0120150 A1 | 6/2003 | Govari |
| 2004/0181155 A1 | 9/2004 | Glukhovsky |
| 2005/0015079 A1* | 1/2005 | Keider .................. 606/27 |
| 2005/0104577 A1 | 5/2005 | Matei et al. |
| 2007/0149883 A1* | 6/2007 | Yesha .................. 600/485 |

FOREIGN PATENT DOCUMENTS

| | | |
|---|---|---|
| EP | 1325708 B1 | 8/2006 |
| JP | 55/114975 | 9/1980 |
| JP | H10/162112 | 6/1998 |
| JP | H10162112 A | 6/1998 |
| JP | 05/114627 | 4/2005 |
| WO | WO 96/05768 A1 | 2/1996 |
| WO | WO 98/11840 A1 | 3/1998 |
| WO | WO 02/071943 A | 9/2002 |

OTHER PUBLICATIONS

Notice of Rejection for corresponding Patent Application No. 2006-193183 dated May 7, 2013.

Reporting Letter for corresponding Patent Application No. 2006-193183 dated Jul. 19, 2013.

* cited by examiner

WIRELESS POSITION TRANSDUCER WITH DIGITAL SIGNALING

FIELD OF THE INVENTION

The present invention relates generally to position sensing systems, and specifically to operation of wireless position transducers.

BACKGROUND OF THE INVENTION

Various methods and systems are known in the art for tracking the coordinates of objects involved in medical procedures. Some of these systems are based on transmission and reception of magnetic fields. In some cases, the fields are transmitted by radiators outside the body and received by sensors fixed to an object within the body; whereas in other cases, radiators on the object within the body transmit fields to receivers outside the body. The basic techniques for computing the coordinates of the object based on the sensed fields are similar in either case.

For example, U.S. Pat. Nos. 5,391,199 and 5,443,489 to Ben-Haim, whose disclosures are incorporated herein by reference, describe systems wherein the coordinates of an intrabody probe are determined using one or more field transducers, such as a Hall effect device, coils, or other antennas. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations. Alternatively, a transmitting antenna in the probe may generate the magnetic fields, which are then sensed by receivers outside the body.

PCT Patent Publication WO 96/05768, U.S. Pat. No. 6,690,963, and U.S. Patent Application Publication 2002/0065455, all to Ben-Haim et al., whose disclosures are incorporated herein by reference, describe a system that generates six-dimensional position and orientation information regarding the tip of a catheter. This system uses a plurality of sensor coils adjacent to a locatable site in the catheter, for example near its distal end, and a plurality of radiator coils fixed in an external reference frame. The sensor coils generate signals in response to magnetic fields generated by the radiator coils, which signals allow for the computation of six location and orientation coordinates.

U.S. Pat. No. 6,239,724 to Doron et al., whose disclosure is incorporated herein by reference, describes a wireless, telemetry system for providing coordinates of an intrabody object. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

U.S. Patent Application Publication 2003/0120150, to Govari, whose disclosure is incorporated herein by reference, describes a system wherein a wireless transponder is fixed to an object. The transponder includes at least one sensor coil, in which a signal current flows responsively to electromagnetic fields generated by fixed radiators, and a power coil, which receives a radio-frequency (RF) driving field and conveys electrical energy from the driving field to power the transponder. The power coil also transmits an output signal responsively to the signal current to a signal receiver, which processes the signal to determine coordinates of the object.

U.S. Pat. No. 5,099,845, to Besz et al., whose disclosure is incorporated herein by reference, describes a medical instrument location determining device, which has a radiating element forming part of the instrument to be inserted into an object (such as a human body). The element radiates a signal, which is detected by at least one receiving element. The received signal energy level is used to measure the distance of the radiating element from the receiving element, which is then indicated to an operator of the instrument so that he can locate the instrument within the object.

U.S. Pat. No. 5,762,064, to Polyani, whose disclosure is incorporated herein by reference, describes a medical magnetic positioning system and method for determining the position of a magnetic probe inside the body. At least two spaced magnetometers are fastened to an area on an external portion of the body proximate to the desired location of the probe inside of the body. The three-dimensional magnetic field of the probe is detected at the magnetometers, and the location of the probe is determined in accordance with the location of the detected three-dimensional field.

SUMMARY OF THE INVENTION

In the embodiments of the present invention that are described hereinbelow, a miniature, wireless position transducer is fixed to an object that is inserted into the body of a patient. The transducer may be contained in an implant, for example, or attached to a tool that is used to perform a surgical procedure on the patient. The position transducer generates a magnetic field, which is detected by receivers at fixed locations, typically (although not necessarily) outside the patient's body. In response to the detected field, the receivers output position signals, which are analyzed in order to determine coordinates of the transducer, and hence of the object inside the body.

In some embodiments of the present invention, the position transducer comprises a digital microcontroller, which controls the operation of the transducer. The microcontroller is coupled to drive one or more transmit antennas, such as coil antennas, to generate the magnetic field. In order to make the transducer as small and as simple as possible, the antennas are coupled directly to the output pins of the microcontroller, i.e., without an additional analog amplifier intervening between the microcontroller and the coils. The microcontroller is programmed to output an alternating digital output, such as a square wave, between these pins at the desired driving frequency. As a result, the antennas generate magnetic fields at the driving frequency, and the receivers can be tuned to detect the fields at this frequency. In one embodiment, three coils, wound in different directions, are driven by different pins of the microcontroller in order to transmit three different, distinguishable fields.

In some embodiments of the present invention, the microcontroller is configured to receive digital data via wireless downlink, so as to permit external control and reprogramming while the transducer is inside the body. For this purpose, a radio-frequency (RF) carrier is transmitted toward the transducer from an antenna outside the body. The carrier is amplitude-modulated in order to convey data to the sensor. The carrier is received by an antenna, such as a coil in a resonant circuit, which is connected through a rectifier directly to an input pin of the microcontroller. No amplifier or analog/digital (A/D) converter is required in this receiver circuit. Rather, the microcontroller simply senses the level of the envelope as provided by the rectifier.

In one embodiment, the wireless downlink is used to transmit a frequency synchronization signal to the position transducer, by modulating the high-frequency carrier signal at the desired driving frequency of the magnetic field to be generated by the transducer. The microcontroller drives the transmit antenna in precise synchronization with the modulated carrier signal. The receivers outside the body are tuned to the frequency (and possibly the phase) of the synchronization signal, and can thus reliably detect the weak fields transmitted by the position transducer, even in the presence of substantial background noise. The digitally-controlled transducer thus achieves precise frequency and phase control with minimal additional circuitry and without the need for costly frequency-control components in the transducer.

In some embodiments of the present invention, power for the digital microcontroller is supplied inductively from a radio frequency (RF) radiator outside the body. The RF power causes current to flow in one or more power coils in the transducer unit. The current is rectified, and the rectified current is input to a regulator, which supplies the appropriate DC voltage to the microcontroller.

In one embodiment, the microcontroller comprises a programmable, non-volatile memory, such as a flash memory. In order to reprogram the memory while the transducer is inside the patient's body, the input voltage level to the microcontroller is switched from a normal operating voltage to a higher voltage level required for programming. The voltage level switching can be accomplished using a simple, fixed-output regulator, which is connected to a switchable input pin of the microcontroller. The microcontroller internally switches this input pin so that the ground output pin of the regulator may alternately be grounded or may float above ground by a selected voltage. Floating the regulator ground pin increases the voltage input level to the microcontroller, thus permitting the memory to be reprogrammed with digital data transmitted via wireless downlink to the transducer. A similar technique may be used for remote programming when the transducer comprises a battery as its power source, rather than induced RF power.

There is therefore provided, in accordance with an embodiment of the present invention, apparatus for tracking an object, including:

a position transducer, which is adapted to be fixed to the object, and which includes:

a digital microcontroller, including a plurality of output pins, and which is operative to generate an alternating digital output at a selected frequency on at least one of the output pins; and     at least one transmit antenna coupled directly to the at least one of the output pins, so that the at least one antenna transmits a magnetic field at the selected frequency responsively to the alternating digital output;

a field sensor, which is adapted to sense the magnetic field and to generate a signal responsively thereto; and a processor, which is coupled to receive and process the signal in order to determine coordinates of the position transducer.

In disclosed embodiments, the at least one transmit antenna includes a coil, having a resonant frequency in a vicinity of the selected frequency. Typically, the plurality of the output pins of the digital microcontroller includes at least first and second output pins, and the coil is coupled directly between the first and second output pins. The digital microcontroller may be operative to generate first and second alternating digital outputs of opposite phases at the selected frequency on the first and second output pins, respectively.

In a disclosed embodiment, the alternating digital output includes a square wave.

In some embodiments, the plurality of output pins includes at least first and second output pins, and the at least one transmit antenna includes at least first and second antenna coils, which are respectively coupled directly to the first and second output pins, and the digital microcontroller is operative to generate the alternating digital output on the first and second output pins so as drive the first and second antenna coils in alternation. In one embodiment, the plurality of output pins includes an additional output pin, and the first and second antenna coils are coupled directly between the additional output pin and the first and second output pins, respectively. Typically, the at least first and second antenna coils are wound on mutually-orthogonal axes.

In some embodiments, the apparatus includes a reference transmitter, which is operative to transmit a radio-frequency (RF) signal, which is modulated so as convey binary data to the position transducer, wherein the position transducer includes a receive antenna, which is adapted to receive the signal, and a demodulation circuit, which is coupled to the receive antenna so as to demodulate and pass the binary data to the digital microcontroller, and wherein the digital microcontroller is adapted to generate the alternating digital output responsively to the binary data. In a disclosed embodiment, the RF signal is amplitude modulated responsively to the binary data at a predetermined data rate, and the digital microcontroller includes a digital input pin, and the demodulation circuit includes a rectifier, which is connected directly between the receive antenna and the digital input pin, so as to rectify the RF signal and to couple the rectified RF signal to the digital input pin. Typically, the binary data include a synchronization signal.

In some embodiments, the apparatus includes a power transmitter, which is operative to transmit radio-frequency (RF) energy to the position transducer, wherein the position transducer includes at least one receive antenna, which is adapted to receive the transmitted RF energy, and a rectifier, which is coupled to rectify the RF energy to provide a direct current (DC) input to the digital microcontroller.

In a disclosed embodiment, the position transducer is a wireless device, which is encapsulated for insertion into a body of a subject. Optionally, the position transducer includes at least one additional sensor for sensing a physiological parameter in the body, and the at least one addition sensor is connected to the microcontroller for transmission of sensor readings thereby via the at least one transmit antenna.

There is also provided, in accordance with an embodiment of the present invention, apparatus for tracking an object, including:

a reference transmitter, which is operative to transmit a radio-frequency (RF) signal, which is modulated at a reference frequency;

a position transducer, which is adapted to be fixed to the object, and which includes:

at least one antenna, for receiving the RF signal and for transmitting a magnetic field; and     a digital microcontroller, which is coupled to the at least one antenna so as to receive the reference frequency from the RF signal, and to drive the at least one antenna to generate the magnetic field at the reference frequency;

a field sensor, which is tuned to sense the magnetic field at the reference frequency and is adapted to generate a signal responsively thereto; and a processor, which is coupled to receive and process the signal in order to determine coordinates of the position transducer.

In a disclosed embodiment, the digital microcontroller includes a digital input pin, and the position transducer includes a rectifier, which is connected directly between the at least one antenna and the digital input pin, so as to rectify the RF signal and to couple the rectified RF signal to the digital input pin.

Additionally or alternatively, the digital microcontroller is operative to drive the at least one antenna to generate the magnetic field in a predetermined phase relation with the modulated RF signal, and the field sensor is adapted to sense the magnetic field responsively to the phase relation.

In a disclosed embodiment, the digital microcontroller includes input and output pins, and wherein the at least one antenna includes a receive antenna, which is coupled to at least one of the input pins, and a transmit antenna, which is coupled to at least one of the output pins. Typically, the digital microcontroller is operative to drive the transmit antenna by generating a square wave at the reference frequency on the at least one of the output pins.

There is additionally provided, in accordance with an embodiment of the present invention, a wireless device, including:

a digital microcontroller, including a digital input pin which is adapted to receive binary data;

a receive antenna, which is adapted to receive a radio-frequency (RF) signal, which is amplitude-modulated at a predetermined modulation rate so as convey the binary data to the wireless device; and a rectifier, which is connected directly between the receive antenna and the digital input pin, so as to rectify the RF signal and to couple the rectified RF signal to the digital input pin.

In a disclosed embodiment, the rectifier includes a single diode, connected in series between the receive antenna and the digital input pin.

Typically, the RF signal has a carrier frequency, and wherein the receive antenna includes a coil, having a resonance in a vicinity of the carrier frequency.

In one embodiment, the digital microcontroller is configured so that appearance of the rectified RF signal on the digital input pin triggers an interrupt in the digital microcontroller.

In some embodiments, the device includes a transmit antenna, wherein the digital microcontroller includes a digital output pin, which is coupled to drive the transmit antenna to transmit a magnetic field responsively to the binary data. Typically, the digital microcontroller is adapted to generate a square wave on the digital output pin in synchronization with the modulation rate of the binary data.

There is further provided, in accordance with an embodiment of the present invention, a wireless device, including:

a power source, which is adapted to generate a direct-current (DC) voltage;

a regulator, which includes a power input connected to the power source, a power output, and a ground output, and which is operative to generate a first voltage between the power and ground outputs responsively to the DC voltage;

a diode, including a first terminal connected to the ground output of the regulator and including a second terminal;

a digital microcontroller, which includes:
  a non-volatile memory, which is accessible in a read-only mode when operated at the first voltage, and which is programmable when operated at a second voltage, higher than the first voltage;
  a power input, which is connected to the power output of the regulator;
  a ground pin, which is connected to the second terminal of the diode;
  an input pin, which is switchable by the microcontroller between a first configuration in which the input pin is connected to the ground pin and a second configuration in which the input pin floats; and
  a data input, which is coupled to receive a data signal transmitted over the air, the data signal including a programming command and data, wherein the microcontroller is adapted, responsively to the programming command, to switch the input pin from the first to the second configuration, thereby causing the voltage between the power input and the ground pin to increase to the second voltage, and to write the data to the non-volatile memory while the input pin is in the second configuration.

In a disclosed embodiment, the digital microcontroller is adapted, responsively to the data, to transmit a signal for use in determine coordinates of the wireless device.

In one embodiment, the non-volatile memory includes a flash memory.

Typically, the data signal includes a radio-frequency (RF) signal, which is modulated so as convey binary data to the device, and the device includes a receive antenna, which is adapted to receive the RF signal, and a demodulation circuit, which is coupled to the receive antenna so as to demodulate and pass the binary data to the data input of the digital microcontroller. In a disclosed embodiment, the RF signal includes a RF carrier, which is amplitude-modulated responsively to the binary data, and the demodulation circuit includes a rectifier, which is connected directly between the receive antenna and the digital input pin, so as to rectify the RF signal.

There is moreover provided, in accordance with an embodiment of the present invention, a method for tracking an object, including:

fixing a position transducer to the object, the position transducer including a digital microcontroller, which includes a plurality of output pins;

coupling at least one transmit antenna directly to at least one of the output pins;

generating an alternating digital output at a selected frequency on the at least one of the output pins of the digital microcontroller, so as to cause the at least one antenna to transmit a magnetic field at the selected frequency;

sensing the magnetic field in order to determine coordinates of the position transducer.

There is furthermore provided, in accordance with an embodiment of the present invention, a method for tracking an object, including:

transmitting a radio-frequency (RF) signal, which is modulated at a reference frequency, from a reference transmitter;

fixing a position transducer to the object, the position transducer including at least one antenna, for receiving the RF signal and for transmitting a magnetic field, and a digital microcontroller, which is coupled to the at least one antenna so as to receive the reference frequency from the RF signal, and to drive the at least one antenna to generate the magnetic field at the reference frequency;

sensing the magnetic field at the reference frequency in order to determine coordinates of the position transducer.

There is also provided, in accordance with an embodiment of the present invention, a method for operating a wireless device that includes a digital microcontroller, the method including:

transmitting a radio-frequency (RF) signal, which is amplitude-modulated at a predetermined modulation rate so as convey binary data to the wireless device;

coupling a receive antenna to the digital microcontroller by connecting a rectifier directly between the receive antenna and the digital input pin, so as to rectify the RF signal and to couple the rectified RF signal to the digital input pin.

The present invention will be more fully understood from the following detailed description of the embodiments thereof, taken together with the drawings in which:

DETAILED DESCRIPTION OF EMBODIMENTS

Figure 1:
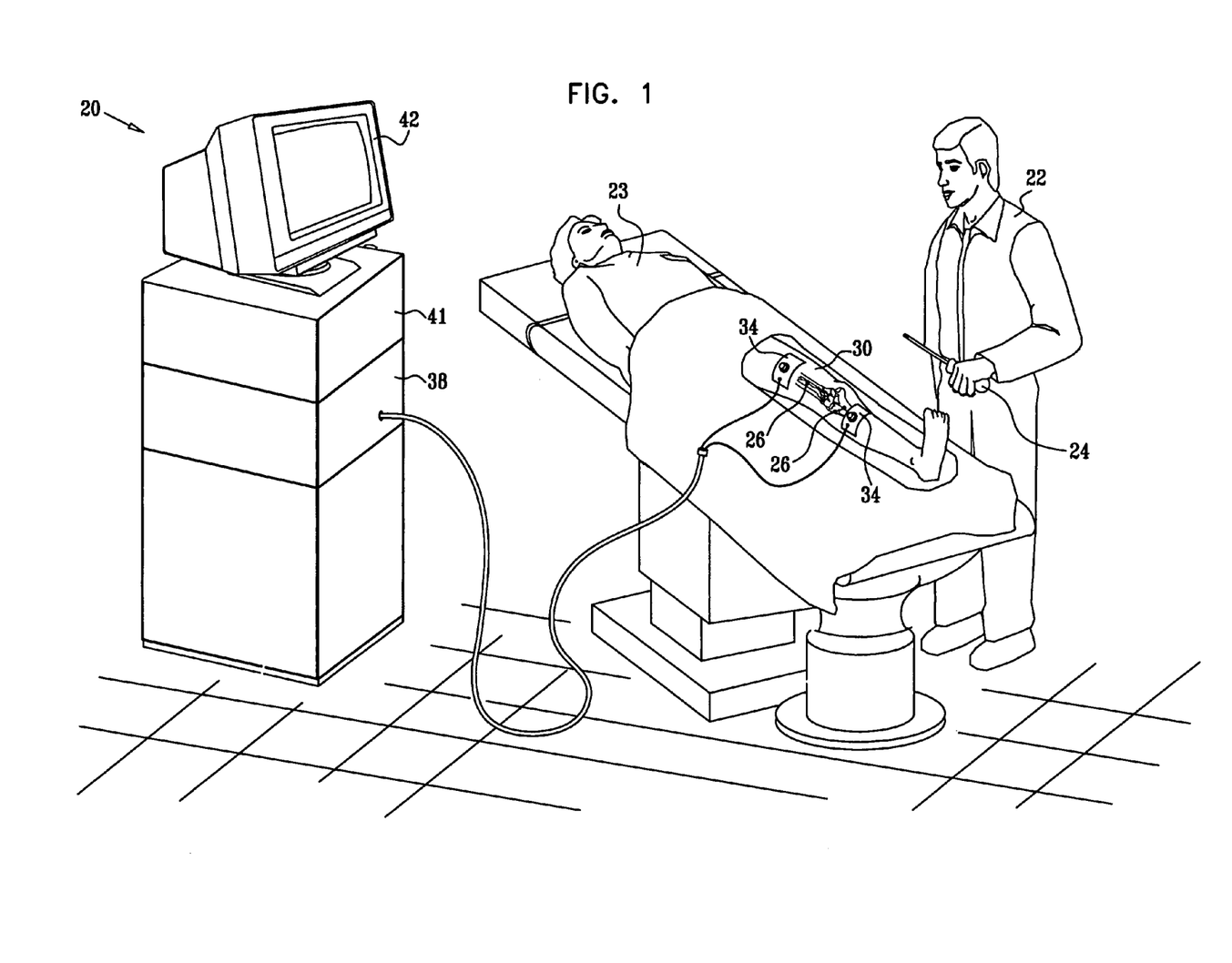
FIG. 1 is a schematic, pictorial illustration of a system for position sensing, in accordance with an embodiment of the present invention.

FIG. 1 is a schematic, pictorial illustration of a magnetic tracking system 20 used in surgery, in accordance with an embodiment of the present invention. A surgeon 22 performs a medical procedure on a patient 23 using a tool 24. Implants 26 are introduced into the patient's body at a surgical site, which is located in this example in a leg 30 of the patient. The tracking system guides the surgeon in performing the procedure, in this example a knee-joint operation, by measuring and presenting the positions of implants 26 and tool 24. The system measures the location and orientation coordinates throughout a working volume that comprises the surgical site.

Implants 26 and tool 24 contain miniature, wireless position transducers, which are described in detail hereinbelow. Each position transducer comprises one or more transmit antennas, typically coils, which are driven to generate magnetic fields. The coordinates of tool 24 and implants 26 are determined relative to field sensors, such as location pads 34, which are fixed to the patient's body and sense the magnetic fields generated by the position transducers. In the example shown in FIG. 1, the pads are placed on the patient's calf and thigh, in proximity to implants 26. The location pads comprise sensing antennas, such as coils, as shown below in FIG. 2. Alternatively or additionally, the field sensors may be fixed to the operating table or to another structure in the vicinity of patient 23.

The magnetic fields generated by the position transducers in tool 24 and implants 26 induce currents in location pads 34, which are indicative of the location and orientation of the position transducers relative to the sensing antennas. In response to the induced currents (or corresponding voltages), the location pads transmit position signals to a signal processing console 38. The console processes the received signals in order to calculate location and orientation coordinates of tool 24 and implants 26. A computer 41 (which may also perform the functions of console 38) presents the position information graphically to the surgeon on a display 42. For example, the display may show the location and orientation of tool 24 relative to implants 26 as surgeon 22 manipulates the tool during the surgical procedure.

Although the use of system 20 is shown, for the sake of illustration, in the context of orthopedic surgery, the principles of the present invention may similarly be applied in other wireless position sensing systems and applications. For example, wireless position transducers of the type described herein may be incorporated in other types of medical implants and tools, such as catheters for cardiovascular applications, and may likewise be used in non-medical applications.

Figure 2:
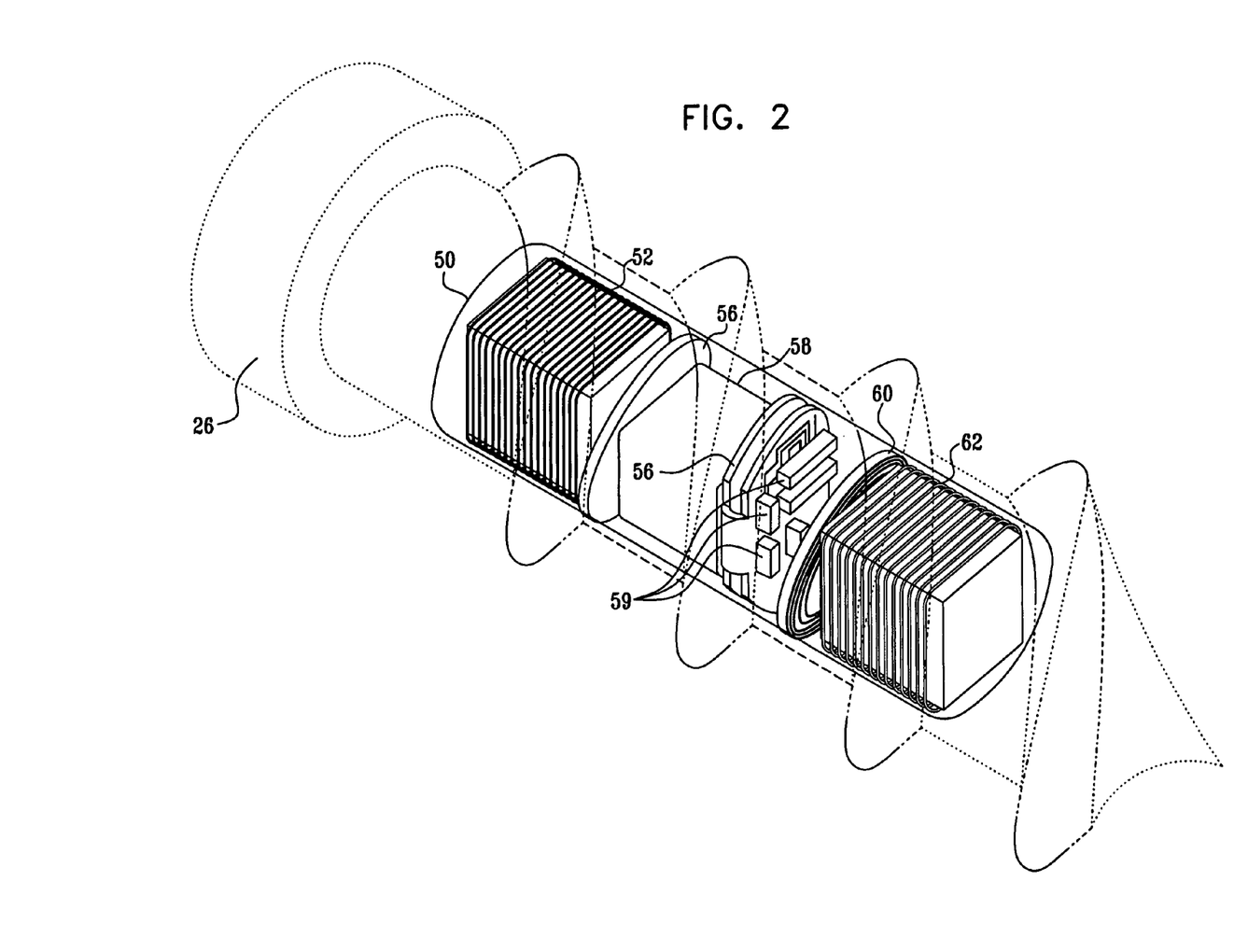
FIG. 2 is a schematic, pictorial illustration showing details of a position transducer, in accordance with embodiments of the present invention.

FIG. 2 is a schematic, pictorial illustration of a position transducer 50 that is encapsulated in implant 26, in accordance with an embodiment of the present invention. Alternatively, transducer 50 may be contained in or otherwise attached to other types of implants, tools and other invasive devices. Transducer 50 in this exemplary embodiment comprises one or more transmitter coils 52, which typically comprises coil wires wound on a magnetic core. Transducer 50 further comprises one or more power coils 62, and a wireless communication coil 60. The coils are mounted on a suitable substrate 56, such as a flexible printed circuit board (PCB), and are coupled to a microcontroller 58 and peripheral circuit elements 59, which are likewise mounted on the substrate. Microcontroller 58 may comprise, for example, one of the MSP430 family of ultra-low-power 16-bit RISC mixed-signal processors, produced by Texas Instruments (Dallas, Tex.). Transducer 50 is typically encapsulated within the implant so as to prevent contact between the elements of the transducer and tissues and body fluids of the patient.

Microcontroller 58 drives transmitter coils 52 to generate the magnetic fields that are sensed by location pads 34, as described hereinbelow. The microcontroller is powered by radio frequency (RF) energy received by power coils 62, and is controlled using control signals received by communication coil 60. Typically, the RF energy and control signals are transmitted by location pads 34, in addition to the role of the location pads in sensing the magnetic fields generated by transmitter coils 52. Alternatively or additionally, the RF power and communication signals may be transmitted to transducer 50 from another source. Further alternatively or additionally, transducer 50 may comprise a battery (not shown) for powering the microcontroller. As another option, the microcontroller may operate independently, based on microcode stored in a memory in the transducer, without any communication input.

Although for simplicity, FIG. 2 shows only a single coil in each of the transmitter and power coil assemblies, in practice each assembly typically comprises multiple coils, such as three transmit coils and three power coils. The transmit coils may be wound together, in mutually-orthogonal directions, on one core, while the power coils are wound together, in mutually-orthogonal directions, on another core. Alternatively, the transmit and power coils may be overlapped on the same core, as described, for example in U.S. patent application Ser. No. 10/754,751, filed Jan. 9, 2004, whose disclosure is incorporated herein by reference.

Figure 3:
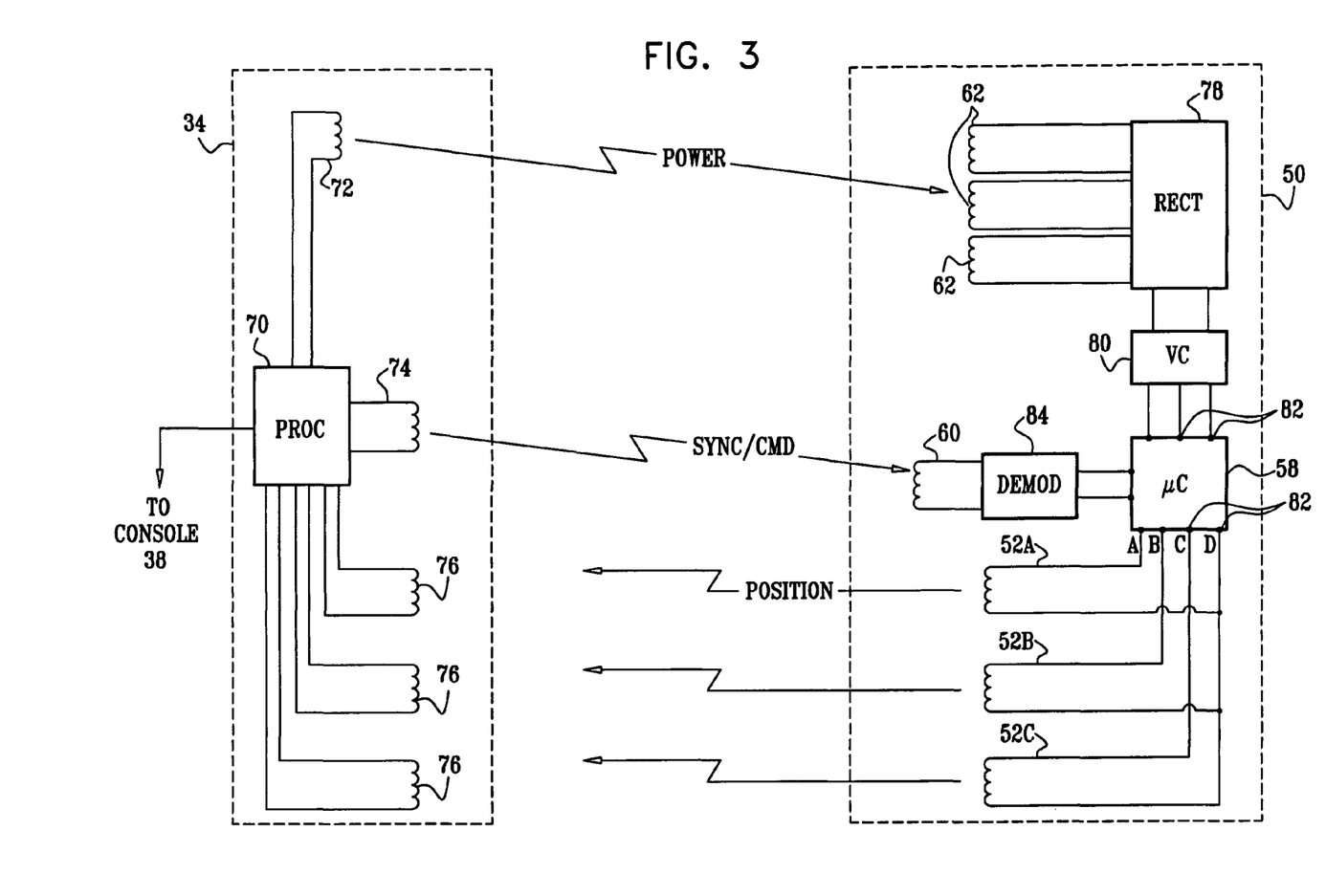
FIG. 3 is a block diagram that schematically shows functional elements of a position sensing system, in accordance with an embodiment of the present invention.

FIG. 3 is a block diagram that schematically shows functional elements of location pad 34 and position transducer 50, in accordance with an embodiment of the present invention. Location pad 34 comprises a processing unit 70, which communicates with console 38. The processing unit drives a power transmission antenna 72 to transmit RF power to power coils 62, and also drives a communication antenna 74 to transmit synchronization and control signals to communication coil 60. Alternatively, as noted above, these functions may be performed by other transmitters (not shown) in system 20, or they may be foregone altogether.

Sensing coils 76 sense the magnetic fields generated by transmit coils 52A, 52B and 52C (referred to collectively as transmit coils 52) in transducer 50. Processing unit 70 filters, amplifies and digitizes the signals induced in sensing coils 76 in order to derive the position signals that are conveyed to console 38. As noted above, the transmit coils are typically wound in mutually-orthogonal directions in order to generate magnetic fields with different spatial orientations. Similarly, sensing coils 76 may be wound in mutually-orthogonal directions in order to give directional resolution of the fields that they sense. Alternatively, different numbers and configurations of transmit coils and sensing coils may be used. For example, to save space and reduce the complexity of transducer 50, the transducer may comprise only one or two transmit coils. Additionally or alternatively, the transmit coils and/or the sensing coils may be non-concentric, and each coil may be wound on a different core. Other coil configurations will be apparent to those skilled in the art.

The RF energy received by power coils 62 is rectified by a rectifier 78, which thus generates a DC input to a voltage control circuit 80. This circuit is coupled to provide a regulated voltage to appropriate pins 82 of microcontroller 58. The input voltage to the microcontroller may be varied, as described hereinbelow with reference to FIG. 7.

Synchronization and control signals from communication coil 60 are demodulated by a demodulation circuit 84, which outputs a binary, amplitude-modulated signal to other pins 82 of the microcontroller. Operation of the demodulation circuit is described hereinbelow with reference to FIGS. 5 and 6. Although only a single communication coil is shown in FIG. 3, transducer 50 may alternatively comprise two or three communication coils, which may be wound in orthogonal directions. These coils may all be connected in parallel or in series to the demodulation circuit.

Still other pins 82 (marked A, B, C, D in FIG. 3) are coupled to drive transmit coils 52A, 52B and 52C. Each of the transmit coils is coupled between a respective pin (A, B or C) and a common pin D. These pins are typically general-purpose input/output (GPIO) pins, which may be set by the microcontroller to either a high (binary 1) or low (binary 0) voltage value under software control. In the embodiment shown in FIG. 3, these pins are coupled directly to coils 52A, 52B and 52C without intervening active components, such as amplifiers external to the microcontroller chip.

Figure 4:
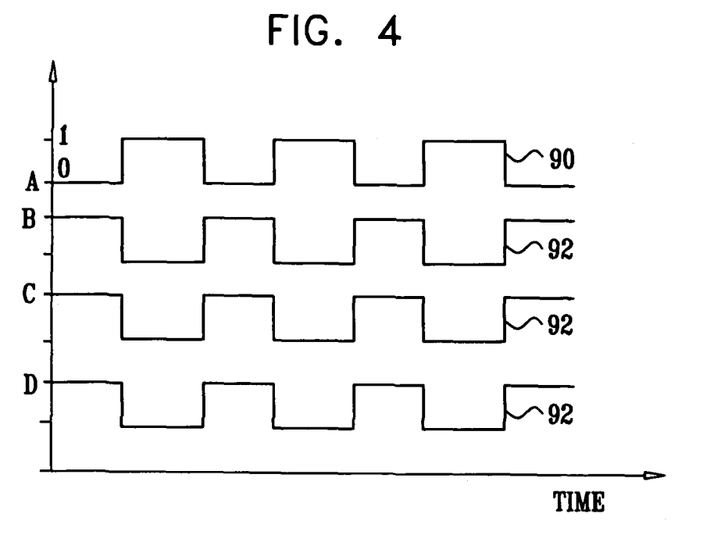
FIG. 4 is a plot that schematically shows drive signals generated by a microcontroller in a position transducer, in accordance with an embodiment of the present invention.

FIG. 4 is a plot that schematically shows drive signals 90, 92, which are generated by microcontroller 58 on pins A, B, C and D, in accordance with an embodiment of the present invention. In this embodiment, the microcontroller pins are driven, in accordance with program instructions, to generate square waves at the desired transmission frequency. Typically the frequency is in the audio range, for example, around 5 kHz, but higher or lower frequency ranges may alternatively be used. Alternatively, if the microcontroller has appropriate computational and digital I/O capabilities, it may generate other forms of alternating digital output, such as an output that approximates a triangular or sinusoidal wave. Transmit coils 52 (along with the wires leading to the coils and possibly other passive components attached to the microcontroller pins) are designed to have resonant frequencies in the vicinity of the transmission frequency, while filtering out higher frequencies. As a result, the transmit coils smooth the square wave signals shown in FIG. 4 into a form that is approximately sinusoidal.

Sensing coils 76 detect the resultant sinusoidal magnetic fields. The absence of an external amplifier between the microcontroller pins and the coils means that the fields are weak, and it is therefore desirable that location pads 34 be located in close proximity to transducers 50. On the other hand, the frequency of the transmitted fields may be controlled very precisely, so that sensing coils 76 may advantageously have very high Q and be tuned precisely to the frequency of drive signals 90, 92. A method that may be used advantageously to control the transmission frequency is described hereinbelow with reference to FIGS. 5 and 6.

As shown in FIG. 4, microcontroller 58 may be programmed to drive transmit coils 52 in a push-pull configuration. For this purpose, both sides of each coil are connected to active output pins of the microcontroller, which are driven with signals of opposite polarities. In the example shown in the figure, coil 52A is being driven by applying signal 90 to pin A at one side of the coil, while applying the opposite-polarity signal 92 to pin D, at the other side of the coil. This feature increases the current flowing through the coil and hence the strength of the transmitted signal.

When multiple transmit coils are provided, as shown in FIG. 3, microcontroller 58 may drive the coils in a time-domain multiplexing (TDM) mode, so that each coil transmits in turn in a sequence of pre-assigned time slots. Thus, in the example shown in FIG. 4, while coil 52A is being driven to transmit a magnetic field, non-transmitting coils 52B and 52C (on pins B and C) are driven with signals 92 of the same polarity as the return pin D. As a result, parasitic current flows in coils 52B and 52C, due to pickup from the transmitting coil 52A, are suppressed. Subsequently, each of pins B and C is driven in turn with signal 90 during the assigned time slots, while the remaining pins are driven with signals 92.

Optionally, microcontroller 58 may be programmed to transmit coded messages via the same GPIO pins as are used to generate the magnetic fields. For example, at start-up of system 20, the microcontroller may transmit the sensor ID and calibration parameters. The messages are received by console 38 via sensing coils 76.

Figure 5:
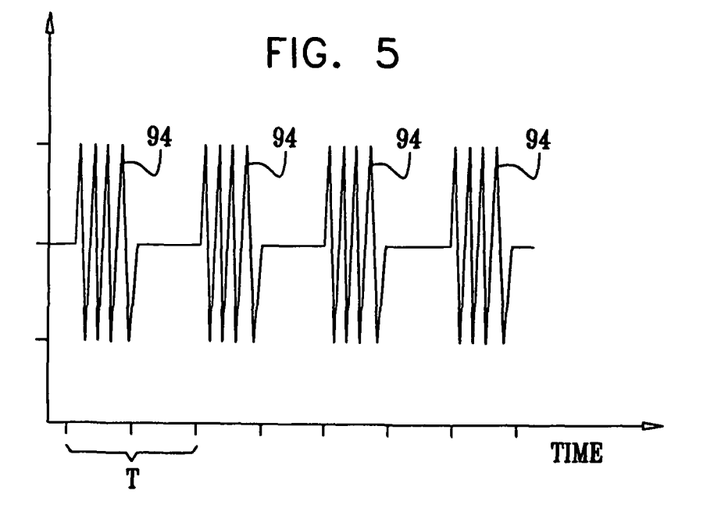
FIG. 5 is a plot that schematically shows an amplitude-modulated downlink signal transmitted to a position transducer, in accordance with an embodiment of the present invention.

FIG. 5 is a plot that schematically shows an amplitude-modulated high-frequency signal 94 transmitted by communication antenna 74, in accordance with an embodiment of the present invention. Signal 94 comprises a high-frequency RF carrier, which may typically be in the range of 40 MHz, although higher or lower frequency ranges may also be used. The carrier is amplitude-modulated in order to convey data to the sensor. In the example shown in the figure, the modulation period T is 200 μs, i.e., the carrier is modulated at 5 kHz, which is equal to the exemplary frequency of drive signals 90 and 92 (FIG. 4).

Figure 6:
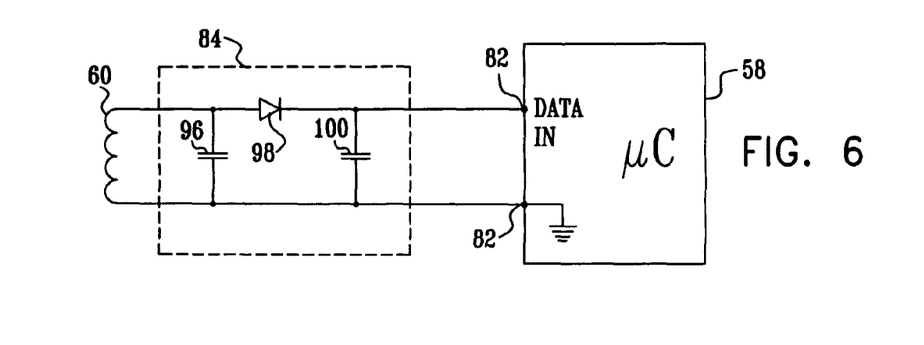
FIG. 6 is an electrical circuit diagram that schematically illustrates a demodulator circuit coupled to a microcontroller, in accordance with an embodiment of the present invention.

FIG. 6 is an electrical circuit diagram that schematically shows details of demodulation circuit 84, in accordance with an embodiment of the present invention. A capacitor 96 is coupled across communication coil 60 to define a resonant circuit, with a resonant frequency at the carrier frequency of signal 94. The coil circuit is connected through a rectifier (such as a diode 98) directly to a pair of pins 82—such as GPIO pins—of microcontroller 58. The demodulation circuit may include a filter, such as a capacitor 100, between the rectifier and the microcontroller. No amplifier, A/D converter or other active component is required, however. Rather, microcontroller 58 simply senses the level of the envelope of signal 94 as provided by demodulation circuit 84.

In the example illustrated by FIGS. 5 and 6, the envelope-modulation of the 40 MHz carrier is used to convey a 5 kHz clock to microcontroller 58. The microcontroller is programmed to drive transmit coils 52 so as to generate magnetic fields at the input clock frequency that it receives from coil 60. Thus, antenna 74 serves as a reference transmitter, and the transmission frequency of transducer 50 is controlled externally by console 38 simply by setting the modulation frequency of the carrier transmitted by antenna 74. This same clock rate is used throughout system 20, so that the filter circuits (not shown) in processing unit 70 can be tuned precisely to this same frequency. No other synchronization is needed. Since all elements of the system are tuned to the same basic frequency, it does not matter if there are small variations in the frequency over time. Furthermore, since the phase relation between the modulation of signal 94 and drive signals 90, 92 is known, processing unit 70 may apply phase-sensitive detection in order to accurately detect the weak magnetic fields generated by transducer 50 even in the presence of substantial background noise.

Although signal 94 as shown in FIG. 5 is simply modulated on and off to convey a timing signal, more complex modulation patterns may be used to convey binary data, as well. (This sort of digital modulation is commonly referred to as amplitude shift keying—ASK.) The data may comprise operational commands to microcontroller 58. Additionally or alternatively, this data channel may be used in reprogramming software code stored in transducer 50, as described hereinbelow.

Typically, microcontroller 58 "sleeps" when transducer 50 is not actively in use for position sensing in system 20. In order to "wake up" the microcontroller when required, the pin of the microcontroller that is connected to receive the demodulated signals from circuit 84 can be chosen so that a signal on this pin generates a specified interrupt. This interrupt causes the microcontroller to start running its operational program and driving coils 52, as described above. Thus, the input data or clock signal itself that is transmitted by antenna 74 causes the transducer to wake up and begin operation.

Figure 7:
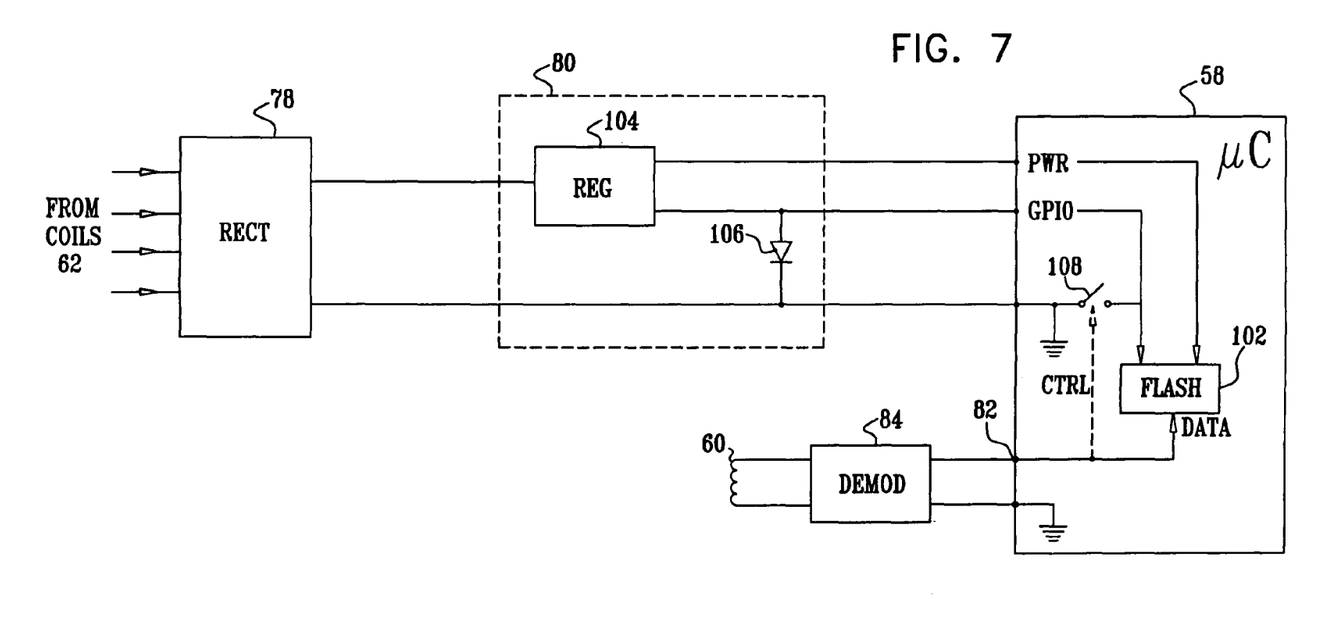
FIG. 7 is a block diagram that schematically illustrates power input and programming control circuits in a position transducer, in accordance with an embodiment of the present invention.

FIG. 7 is a block diagram that schematically illustrates elements of voltage control circuit 80 and microcontroller 58, in accordance with an embodiment of the present invention. Rectifier 78, which typically comprises a full-bridge rectifier with low-pass filter (not shown), outputs a variable DC voltage, depending on the strength of the RF energy received by power coils 62. A DC regulator 104 receives this variable voltage and outputs the fixed voltage level, typically in the range of 2.5 V, that is required to run microcontroller 58. Regulator 104 may comprise, for example, a LP3983 micropower, low quiescent current, CMOS voltage regulator (in a micro-SMD package), produced by National Semiconductor (Santa Clara, Calif.). This regulator provides an output voltage of 2.5 V. The positive voltage output pin of regulator 104 is coupled to the power input pin (PWR) of the microcontroller, while the ground output pin is coupled to a GPIO pin, for reasons explained below. A diode 106 is coupled between this GPIO pin and the a ground pin of the microcontroller. Normally, however, an internal switch 108 in the microcontroller connects the GPIO pin to ground, so that the microcontroller receives the operating voltage level that is output by regulator 104.

Typically, microcontroller 58 comprises a non-volatile read-only memory 102, such as a flash memory, which stores software (microcode) that is used by the microcontroller in operation. Memory 102 may either be on the microcontroller chip, as shown in the figure, or external to the chip. To write to the flash memory, it is necessary to supply the microcontroller with a higher DC voltage than is normally supplied by regulator 104 for operating purposes. In order to provide the increased voltage, switch 108 is opened, as shown in FIG. 7, so that the GPIO pin floats above ground by a voltage equal roughly to the forward voltage drop of diode 106. As a result, a higher voltage (in this example approximately 3.7 V) appears between the PWR input pin and ground. (Additional diodes may be added in series with diode 106 in order to reach higher voltages if necessary.) The higher voltage permits the flash memory to be reprogrammed.

If it is determined during operation of transducer 50 that memory 102 should be reprogrammed, a predetermined sequence of bits is modulated onto the signal transmitted by communication antenna 74. Communication coil 60 receives the signal, and demodulator 84 demodulates and inputs the bit sequence to microcontroller 58. The microprocessor is programmed to recognize that this sequence of bits is a command to enter programming mode. In response to this command, the microprocessor opens switch 108 and thus floats the GPIO pin that is connected to the ground side of regulator 104. The input voltage to the microcontroller increases accordingly. Once in program mode, the microcontroller continues to receive data transmitted by antenna 74 and writes this data to the flash memory, thus overwriting its previous stored program, for example. At the conclusion of the programming sequence, the microcontroller closes switch 108 to ground the GPIO pin and returns to normal operating mode.

Thus, voltage control circuit 80 provides a very simple and economical way for microcontroller 58 to change its own input voltage, using a standard, fixed-voltage regulator as input. No special programming circuitry or high-voltage regulator is required. This aspect of the present invention allows position transducer 50 to be programmed after encapsulation in implant 26, and even allows reprogramming and software upgrades in the field. The principles of this embodiment may be applied in programming of other types of wireless devices, whether powered externally (as in the case of transducer 50) or by internal battery. This method may be used not only for reprogramming microcontroller 58, but also for writing other stored data, such as calibration look-up tables, to flash memory 102.

More generally speaking, although embodiments of the present invention are described hereinabove in the context of a wireless position transducer, aspects of the present invention may be implemented in wireless digital transducers and sensors of other types. For example, the methods and device architecture described above may be used in implantable devices that are used to sense physiological parameters, such as temperature, pressure and/or fluid flow, in addition to position sensing. The microcontroller may then transmit the sensor readings in the manner described above. Alternatively, a separate transmission channel may be provided for transmitting the sensor readings. For example, the readings may be transmitted via a dedicated antenna, separate from the transmit coils 52. Additionally or alternatively, the sensor outputs may be processed by a separate, dedicated microcontroller.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for tracking an object, comprising:
a position transducer, which is adapted to be fixed to the object, and which comprises:
a digital microcontroller, comprising a plurality of output pins, and which is operative to generate an alternating digital output at a selected frequency on at least one of the output pins; and
at least one transmit antenna coupled directly to the at least one of the output pins, so that the at least one antenna transmits a magnetic field at the selected frequency responsively to the alternating digital output, the at least one transmit antenna comprising a coil, having a resonant frequency in a vicinity of the selected frequency;
at least one location pad comprising a field sensor, which is adapted to sense the magnetic field and to generate a signal responsively thereto; and
a processor, which is coupled to receive and process the signal in order to determine location and orientation coordinates of the position transducer.

2. The apparatus according to claim 1, wherein the at least one transmit antenna comprises a coil, and wherein the plurality of the output pins of the digital microcontroller comprises at least first and second output pins, and wherein the coil is coupled directly between the first and second output pins.

3. The apparatus according to claim 2, wherein the digital microcontroller is operative to generate first and second alternating digital outputs of opposite phases at the selected frequency on the first and second output pins, respectively.

4. The apparatus according to claim 1, wherein the alternating digital output comprises a square wave.

5. The apparatus according to claim 1, wherein the plurality of output pins comprises at least first and second output pins, and wherein the at least one transmit antenna comprises at least first and second antenna coils, which are respectively coupled directly to the first and second output pins, and wherein the digital microcontroller is operative to generate the alternating digital output on the first and second output pins so as drive the first and second antenna coils in alternation.

6. The apparatus according to claim 5, wherein the plurality of output pins comprises an additional output pin, and wherein the first and second antenna coils are coupled directly between the additional output pin and the first and second output pins, respectively.

7. The apparatus according to claim 5, wherein the at least first and second antenna coils are wound on mutually-orthogonal axes.

8. The apparatus according to claim 1, and comprising a reference transmitter, which is operative to transmit a radio-frequency (RF) signal, which is modulated so as convey binary data to the position transducer,
wherein the position transducer comprises a receive antenna, which is adapted to receive the signal, and a demodulation circuit, which is coupled to the receive antenna so as to demodulate and pass the binary data to the digital microcontroller, and
wherein the digital microcontroller is adapted to generate the alternating digital output responsively to the binary data.

9. The apparatus according to claim 8, wherein the RF signal is amplitude modulated responsively to the binary data at a predetermined data rate, and wherein the digital microcontroller comprises a digital input pin, and wherein the demodulation circuit comprises a rectifier, which is connected directly between the receive antenna and the digital input pin, so as to rectify the RF signal and to couple the rectified RF signal to the digital input pin.

10. The apparatus according to claim 8, wherein the binary data comprise a synchronization signal.

11. The apparatus according to claim 1, and comprising a power transmitter, which is operative to transmit radio-frequency (RF) energy to the position transducer,
wherein the position transducer comprises at least one receive antenna, which is adapted to receive the transmitted RF energy, and a rectifier, which is coupled to rectify the RF energy to provide a direct current (DC) input to the digital microcontroller.

12. The apparatus according to claim 1, wherein the position transducer is a wireless device, which is encapsulated for insertion into a body of a subject.

13. The apparatus according to claim 12, wherein the position transducer comprises at least one additional sensor for sensing a physiological parameter in the body, and wherein the at least one addition sensor is connected to the microcontroller for transmission of sensor readings thereby via the at least one transmit antenna.

14. Apparatus for tracking an object, comprising:
a reference transmitter, which is operative to transmit a radio-frequency (RF) signal, which is modulated at a reference frequency;
a position transducer, which is adapted to be fixed to the object, and which comprises:
at least one antenna, for receiving the RF signal and for transmitting a magnetic field; and
a digital microcontroller, which is coupled to the at least one antenna so as to receive the reference frequency from the RF signal, and to drive the at least one antenna to generate the magnetic field at the reference frequency;
at least one location pad comprising a field sensor, which is tuned to sense the magnetic field at the reference frequency and is adapted to generate a signal responsively thereto; and
a processor, which is coupled to receive and process the signal in order to determine location and orientation coordinates of the position transducer.

15. The apparatus according to claim 14, wherein the digital microcontroller comprises a digital input pin, and wherein the position transducer comprises a rectifier, which is connected directly between the at least one antenna and the digital input pin, so as to rectify the RF signal and to couple the rectified RF signal to the digital input pin.

16. The apparatus according to claim 14, wherein the digital microcontroller is operative to drive the at least one antenna to generate the magnetic field in a predetermined phase relation with the modulated RF signal, and wherein the field sensor is adapted to sense the magnetic field responsively to the phase relation.

17. The apparatus according to claim 14, wherein the digital microcontroller comprises input and output pins, and wherein the at least one antenna comprises a receive antenna, which is coupled to at least one of the input pins, and a transmit antenna, which is coupled to at least one of the output pins.

18. The apparatus according to claim 17, wherein the digital microcontroller is operative to drive the transmit antenna by generating a square wave at the reference frequency on the at least one of the output pins.

19. The apparatus according to claim 14, and comprising a power transmitter, which is operative to transmit radio-frequency (RF) energy to the position transducer, wherein the position transducer comprises at least one receive antenna, which is adapted to receive the transmitted RF energy, and a rectifier, which is coupled to rectify the RF energy to provide a direct current (DC) input to the digital microcontroller.

20. The apparatus according to claim 14, wherein the position transducer is a wireless device, which is encapsulated for insertion into a body of a subject.

21. A method for tracking an object, comprising:
fixing a position transducer to the object, the position transducer comprising a digital microcontroller, which comprises a plurality of output pins;
coupling at least one transmit antenna directly to at least one of the output pins;
generating an alternating digital output at a selected frequency on the at least one of the output pins of the digital microcontroller, so as to cause the at least one antenna to transmit a magnetic field at the selected frequency;
sensing the magnetic field with a field sensor of at least one location pad in order to determine location and orientation coordinates of the position transducer.

22. The method according to claim 21, wherein the at least one transmit antenna comprises a coil, having a resonant frequency in a vicinity of the selected frequency.

23. The method according to claim 22, wherein the plurality of the output pins comprises at least first and second output pins, and wherein the coil is coupled directly between the first and second output pins.

24. The method according to claim 23, wherein generating the alternating digital output comprises generating first and second alternating digital outputs of opposite phases at the selected frequency on the first and second output pins, respectively.

25. The method according to claim 21, wherein generating the alternating digital output comprises generating a square wave.

26. The method according to claim 21, wherein the plurality of output pins comprises at least first and second output pins, and wherein coupling the at least one transmit antenna comprises respectively coupling first and second antennas directly to the first and second output pins, and wherein generating the alternating digital output comprises generating alternating digital outputs on the first and second output pins so as drive the first and second antennas in alternation.

27. The method according to claim 26, wherein the plurality of output pins comprises a third output pin, and wherein coupling the first and second antennas comprises coupling first and second coils directly between the third output pin and the first and second output pins, respectively.

28. The method according to claim 26, wherein the first and second antennas comprise coils, which are wound on mutually-orthogonal axes.

29. The method according to claim 21, and comprising:
transmitting a radio-frequency (RF) signal, which is modulated so as convey binary data, to the position transducer; and
receiving and demodulating the RF signal at the position transducer so as to input the binary data to the digital microcontroller,
wherein generating the square wave comprises producing the square wave responsively to the binary data.

30. The method according to claim 29, wherein transmitting the RF signal comprises modulating an amplitude of the RF signal responsively to the binary data at a predetermined data rate, and
wherein receiving and demodulating the RF signal comprises connecting a rectifier directly between a receive antenna and a digital input pin of the digital microcontroller, so as to rectify the RF signal and to couple the rectified RF signal to the digital input pin.

31. The method according to claim 29, wherein the binary data comprise a synchronization signal, and wherein producing the square wave comprises synchronizing the square wave with the synchronization signal.

32. The method according to claim 21, and comprising transmitting radio-frequency (RF) energy to the position transducer, and receiving and rectifying the transmitted RF energy to provide a direct current (DC) input to the digital microcontroller.

33. The method according to claim 21, and comprising inserting the object, with the position transducer, into a body of a subject.

34. The method according to claim 33, wherein the position transducer comprises at least one additional sensor for sensing a physiological parameter in the body, and wherein the method comprises coupling the at least one addition sensor to the microcontroller for transmission of sensor readings thereby via the at least one transmit antenna.

35. A method for tracking an object, comprising:
transmitting a radio-frequency (RF) signal, which is modulated at a reference frequency, from a reference transmitter;
fixing a position transducer to the object, the position transducer comprising at least one antenna, for receiving the RF signal and for transmitting a magnetic field, and a digital microcontroller, which is coupled to the at least one antenna so as to receive the reference frequency from the RF signal, and to drive the at least one antenna to generate the magnetic field at the reference frequency;
sensing the magnetic field at the reference frequency with a field sensor of at least one location pad in order to determine location and orientation coordinates of the position transducer.

36. The method according to claim 35, wherein the digital microcontroller comprises a digital input pin, and wherein fixing the position transducer comprises connecting a rectifier directly between the at least one antenna and the digital input pin, so as to rectify the RF signal and to couple the rectified RF signal to the digital input pin.

37. The method according to claim 35, wherein fixing the position transducer comprises driving the at least one antenna using the digital microcontroller to generate the magnetic field in a predetermined phase relation with the modulated RF signal, and wherein sensing the magnetic field comprises sensing the magnetic field responsively to the phase relation.

38. The method according to claim 35, wherein the digital microcontroller comprises input and output pins, and wherein the at least one antenna comprises a receive antenna, which is coupled to at least one of the input pins, and a transmit antenna, which is coupled to at least one of the output pins.

39. The method according to claim 38, wherein fixing the position transducer comprises driving the transmit antenna by generating a square wave at the reference frequency on the at least one of the output pins.

40. The method according to claim 35, and comprising transmitting radio-frequency (RF) energy to the position transducer, and receiving and rectifying the transmitted RF energy to provide a direct current (DC) input to the digital microcontroller.

41. The method according to claim 35, and comprising inserting the object, with the position transducer, into a body of a subject.

* * * * *